United States Patent
Yamamoto

(10) Patent No.: US 10,458,952 B2
(45) Date of Patent: Oct. 29, 2019

(54) ULTRASOUND DIAGNOSTIC APPARATUS, ULTRASOUND IMAGE GENERATION METHOD, AND RECORDING MEDIUM

(71) Applicant: FUJIFILM Corporation, Tokyo (JP)

(72) Inventor: Hiroaki Yamamoto, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 330 days.

(21) Appl. No.: 14/670,186

(22) Filed: Mar. 26, 2015

(65) Prior Publication Data

US 2015/0198566 A1 Jul. 16, 2015

Related U.S. Application Data

(63) Continuation of application No. PCT/JP2013/075480, filed on Sep. 20, 2013.

(30) Foreign Application Priority Data

Sep. 27, 2012 (JP) ................... 2012-215250

(51) Int. Cl.
*G01N 29/07* (2006.01)
*A61B 8/08* (2006.01)
(Continued)

(52) U.S. Cl.
CPC ............... *G01N 29/07* (2013.01); *A61B 8/00* (2013.01); *A61B 8/5207* (2013.01);
(Continued)

(58) Field of Classification Search
CPC .................................................. G01N 29/0654
See application file for complete search history.

(56) References Cited

U.S. PATENT DOCUMENTS

2010/0331692 A1* 12/2010 Kakee ...................... A61B 8/06
600/443
2011/0077519 A1* 3/2011 Katsuyama .............. A61B 8/08
600/443
(Continued)

FOREIGN PATENT DOCUMENTS

JP 2011-92686 A 5/2011

OTHER PUBLICATIONS

Duric, Nebojsa, et al. "Detection of breast cancer with ultrasound tomography: First results with the Computed Ultrasound Risk Evaluation (CURE) prototype." Medical physics 34.2 (2007): 773-785.*

(Continued)

*Primary Examiner* — Herbert K Roberts
(74) *Attorney, Agent, or Firm* — Birch, Stewart, Kolasch & Birch, LLP

(57) ABSTRACT

The ultrasound diagnostic apparatus acquires an ultrasound image for examining an inspection object using an ultrasonic beam, and includes a sound velocity determiner configured to determine a sound velocity in the inspection object, and a sound velocity searching range setting section configured to set a range in which a sound velocity is searched by the sound velocity determiner. The sound velocity searching range setting section sets a sound velocity searching range using a sound velocity calculated in a predetermined range with respect to at least one of space and time.

5 Claims, 5 Drawing Sheets

(51) Int. Cl.
*A61B 8/00* (2006.01)
*G01N 29/06* (2006.01)
(52) U.S. Cl.
CPC ... *G01N 29/0654* (2013.01); *G01N 2291/011* (2013.01); *G01N 2291/106* (2013.01)

(56) References Cited

U.S. PATENT DOCUMENTS

2013/0296706 A1  11/2013  Katsuyama
2013/0303912 A1  11/2013  Katsuyama

OTHER PUBLICATIONS

International Search Report issued in PCT/JP2013/075480, dated Oct. 22, 2013.
English translation of the International Preliminary Report on Patentability and Written Opinion of the International Searching Authority (Forms PCT/IB/338, PCT/IB/373 and PCT/ISA/237), dated Apr. 9, 2015, for International Application No. PCT/JP2013/075480.

* cited by examiner

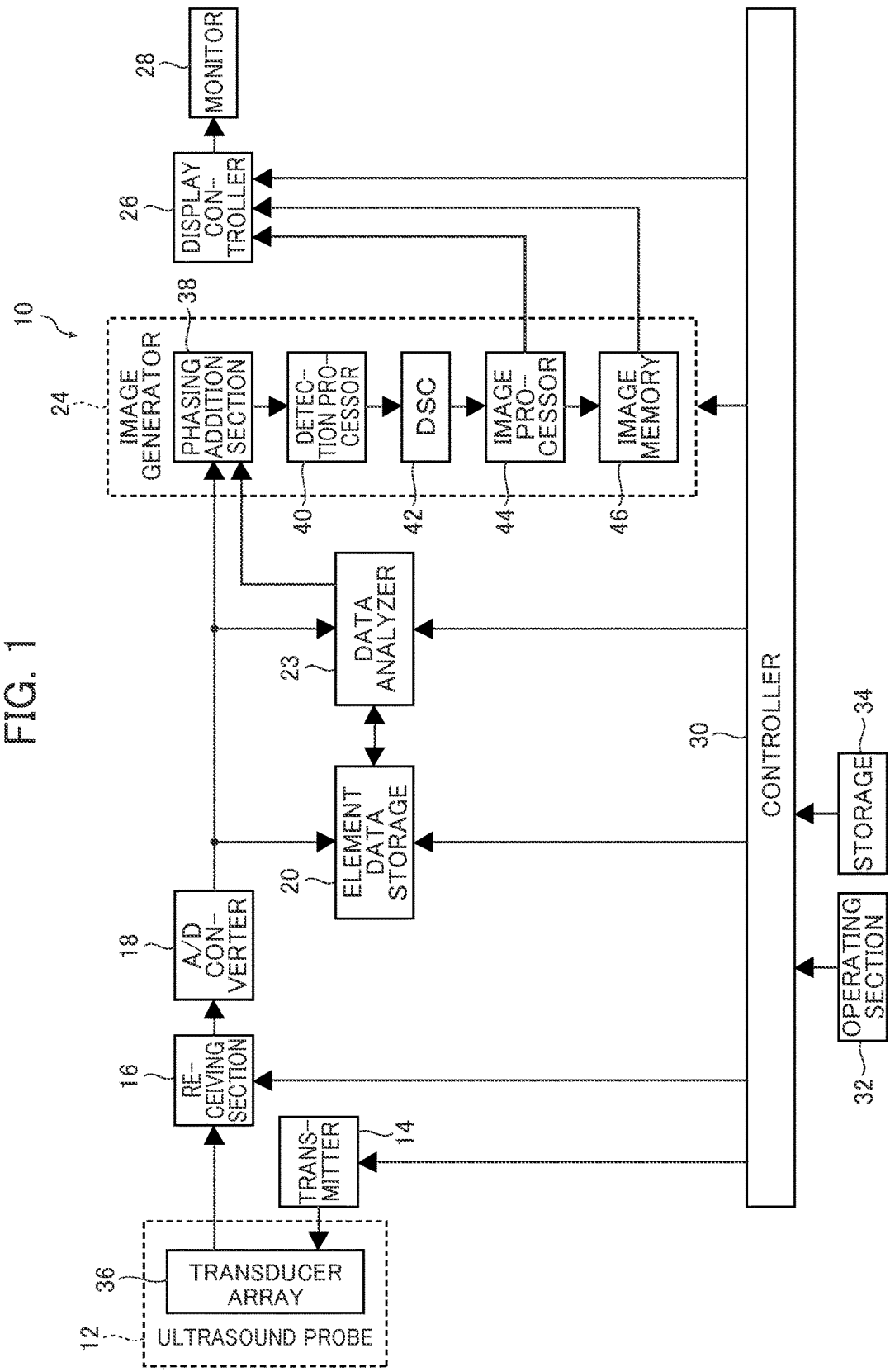

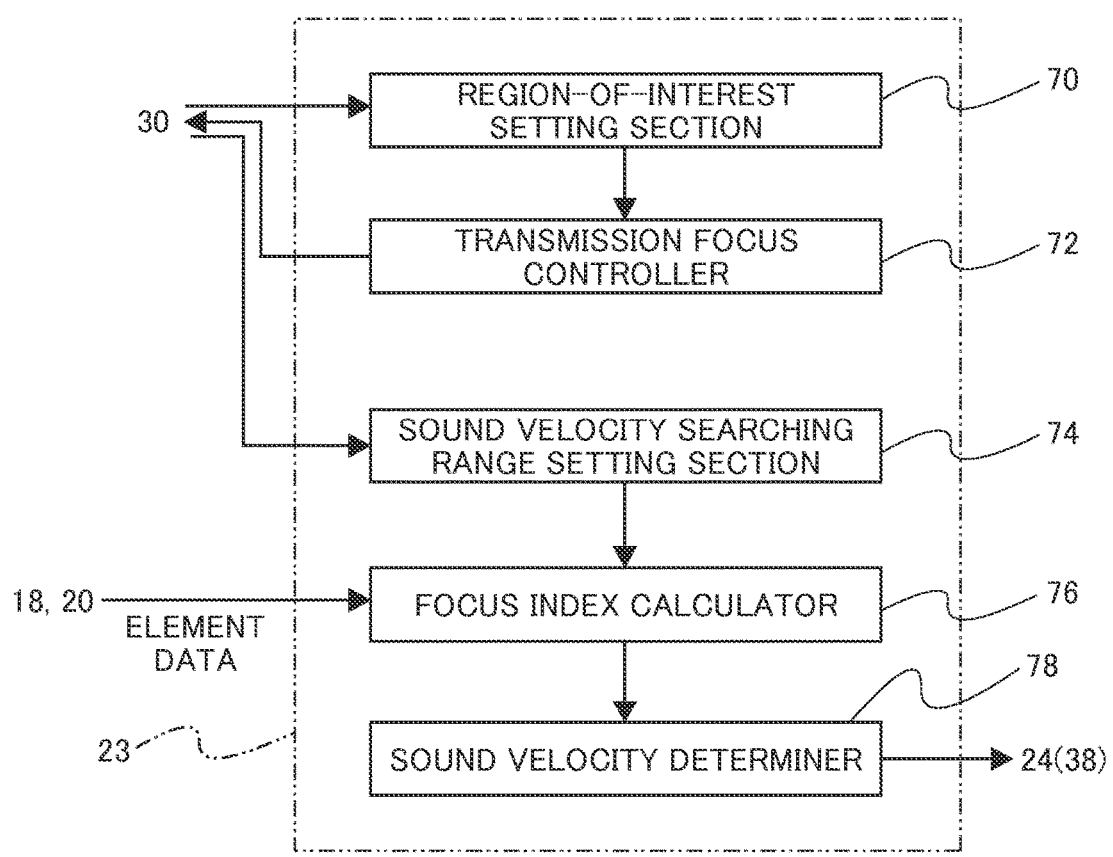

ULTRASOUND DIAGNOSTIC APPARATUS, ULTRASOUND IMAGE GENERATION METHOD, AND RECORDING MEDIUM

CROSS-REFERENCE TO RELATED APPLICATIONS

This application is a Continuation of PCT international Application No. PCT/JP2013/075480 filed on Sep. 20, 2013, which claims priority under 35 U.S.C. § 119(a) to Japanese Application No. 2012-215250 filed on Sep. 27, 2012. Each of the above application(s) is hereby expressly incorporated by reference, in its entirety, into the present application.

BACKGROUND OF THE INVENTION

The invention relates to an ultrasound diagnostic apparatus capable of imaging an inspection object such as an organ in a living body by transmitting and receiving ultrasonic beams so as to generate an ultrasound image used for examination or diagnosis of the inspection object, an ultrasound image generation method, and a recording medium recording a program; and particularly relates to an ultrasound diagnostic apparatus, an ultrasound image generation method, and a recording medium recording a program capable of setting an optimum sound velocity searching range based on a value of a sound velocity calculated previously, reducing sound velocity calculating time, and thus improving a frame rate.

Conventionally, ultrasound examination apparatuses such as ultrasound image diagnostic apparatuses using ultrasound images are put to practical use in the medical field. Generally, an ultrasound examination apparatus of this type has an ultrasound probe including therein a plurality of elements (ultrasound transducers), and an apparatus body connected with the ultrasound probe. Ultrasonic beams are transmitted toward an inspection object (subject) from a plurality of elements of the ultrasound probe, and ultrasonic echoes from the subject are received by the ultrasound probe. Then, the received ultrasonic echo signals are electrically processed in the apparatus body so as to generate an ultrasound image.

When an ultrasound image is generated in the ultrasound examination apparatus, ultrasonic beams are transmitted with a focus on a region to be examined of a subject, e.g., an organ in a living body, a lesion in the organ, or the like from the elements of the probe, and ultrasonic echoes from a reflector body of the region to be examined, e.g., a surface or an interface of the organ, the lesion, or the like are received through the plurality of elements. However, a plurality of elements receive ultrasonic echoes reflected by the same reflector body, and thus as compared with ultrasonic echo signals reflected by the reflector body positioned at a focus position of ultrasonic beams transmitted from a transmission element and received by the transmission element, ultrasonic echo signals reflected by the same reflector body and received by elements other than the transmission element are delayed. Because of this, the ultrasound examination apparatus analog-to-digital (A/D) converts ultrasonic echo signals received by a plurality of elements into element data, and then performs reception focusing processing on element data. That is, the ultrasound examination apparatus performs delay correction to match phases and performs phasing addition to generate sound ray signals, thus generating an ultrasound image based on the obtained sound ray signals.

In conventional ultrasound diagnostic apparatuses, the sound velocity of ultrasonic waves in the subject is assumed to be constant, and reception focusing processing was performed by fixing a sound velocity of the ultrasonic waves to a certain value set in advance.

However, the sound velocity varies depending on the type of tissues such as fatty layers or muscular layers in a living body, and therefore the sound velocity of ultrasonic waves is not uniform in the subject. In addition, the thicknesses of fatty layers or muscular layers are different between an overweight subject and a slim subject. In other words, the sound velocity of ultrasonic waves varies from person to person.

Accordingly, in a conventional ultrasound diagnostic apparatus in which the sound velocity of ultrasonic waves is fixed, when the actual sound velocity in a subject differs from a set sound velocity, the arrival time for the ultrasonic echoes to be reflected inside the subject and reach the elements does not match with a set delay time.

As a result, there is a problem in that proper phase matching is not possible, reception focusing is not properly performed, and the image quality of the obtained ultrasound image becomes inferior. In addition, there is also a problem in that the obtained ultrasound image is distorted with respect to the actual subject.

With respect to such problems, in the ultrasound diagnostic apparatus, the sound velocity in the subject is determined (calculated), and reception focusing processing is performed using this sound velocity.

For example, JP 2011-92686 A describes an ultrasound diagnostic apparatus which transmits and receives ultrasonic waves after setting a region-of-interest where a diagnosis region (in an ultrasound image) is divided, calculates a focus index for each of a plurality of sound velocities (set sound velocities) set in advance in each region-of-interest by performing reception focusing processing with respect to obtained element data using a plurality of sound velocities (set sound velocities) set as appropriate, and uses the calculated focus indexes to determine the sound velocity in the region-of-interest.

Examples of the focus indexes include contrast value, brightness, and the like. For example, a set sound velocity where the brightness set as the focus index was the highest may be determined as the sound velocity in the region-of-interest.

JP 2011-92686 A describes that the delay time correction, the phasing addition, and reception focusing processing is performed based on the sound velocity determined using focus indexes, and then envelope detection processing is performed after correction for attenuation so as to form a brightness image (B mode image).

SUMMARY OF THE INVENTION

In the above JP 2011-92686 A, sound velocity values are searched comprehensively to determine a sound velocity in the region-of-interest. Accordingly, the determination of a sound velocity value in the region-of-interest requires time. The frame rate is also reduced because the determination of a sound velocity value requires time.

An object of the invention is to solve the problems of the conventional art described above and to provide an ultrasound diagnostic apparatus, an ultrasound image generation method, and a recording medium recording a program capable of reducing sound velocity value calculating time.

In order to attain the above-described object, a first aspect of the invention provides an ultrasound diagnostic apparatus acquiring an ultrasound image for examining an inspection object using an ultrasonic beam, the ultrasound diagnostic apparatus including: a sound velocity determiner configured to determine a sound velocity in the inspection object; and a sound velocity searching range setting section configured to set a range in which a sound velocity is searched by the sound velocity determiner; in which the sound velocity searching range setting section sets a sound velocity searching range using a sound velocity calculated in a predetermined range with respect to at least one of space and time.

For example, a sound velocity used for setting the sound velocity searching range is a sound velocity of a region adjacent to a region for which a sound velocity is determined by the sound velocity determiner in an ultrasound image.

For example, a sound velocity used for setting the sound velocity searching range is, upon the ultrasound image being divided into a plurality of regions so as to include a region for which a sound velocity is determined by the sound velocity determiner, a sound velocity of a region different from the region for which a sound velocity is determined by the sound velocity determiner among the plurality of regions.

For example, the ultrasound diagnostic apparatus further includes a storage configured to store an ultrasound image having stored sound velocities of regions, for every one frame and for one or more predetermined previous frames, in which a sound velocity used for setting the sound velocity searching range is any one of a sound velocity of a region for which a sound velocity is determined by the sound velocity determiner, and a sound velocity of a region corresponding to an ultrasound image of at least one predetermined previous frame stored in the storage, and a sound velocity of a region corresponding to a sound velocity of each region of at least one ultrasound image obtained by performing predetermined processing on sound velocities of each region of an ultrasound image of one or more predetermined previous frames stored in the storage. The predetermined processing is, for example, calculation of any one of an average value and a median of sound velocities of each region of an ultrasound image of one or more predetermined pervious frames stored in the storage.

A second aspect of the invention provides an ultrasound image generation method for acquiring an ultrasound image for examining an inspection object using an ultrasonic beam, the ultrasound image generation method including the steps of: determining a sound velocity with respect to at least one region in the inspection object; and setting, upon determination of a sound velocity of another region, a sound velocity searching range using a sound velocity calculated in a predetermined range with respect to at least one of space and time.

A third aspect of the invention provides a computer-readable recording medium recording a program causing a computer to execute the steps of the ultrasound image generation method according to the second aspect of the invention.

According to the ultrasound diagnostic apparatus and the ultrasound diagnostic method of the invention, it is possible to reduce sound velocity value calculating time and thus improve a frame rate by setting an optimum sound velocity searching range based on a sound velocity value obtained previously.

BRIEF DESCRIPTION OF THE DRAWING

FIG. 1 is a block diagram conceptually illustrating an example of a configuration of an ultrasound diagnostic apparatus of the invention.

FIG. 2 is a block diagram conceptually illustrating an example of a configuration of a data analyzer of the ultrasound diagnostic apparatus illustrated in FIG. 1.

DETAILED DESCRIPTION OF THE INVENTION

Figure 3A:
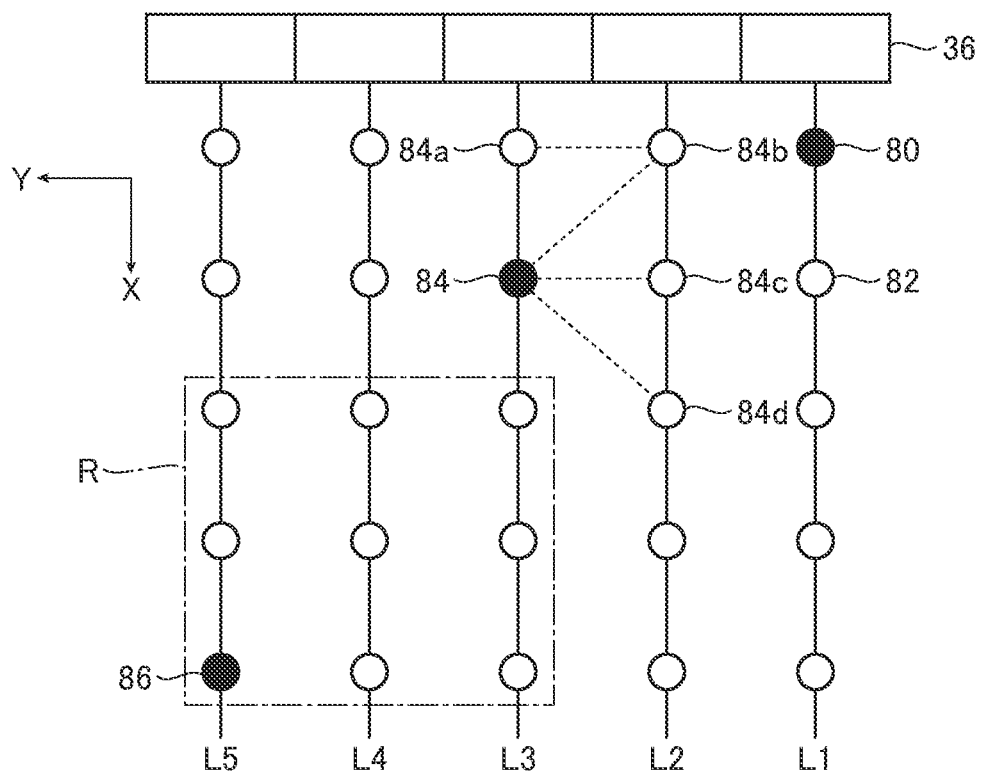
FIG. 3A is a schematic view for illustrating an example of resetting of a sound velocity searching range.

An ultrasound diagnostic apparatus, an ultrasound image generation method, and a recording medium recording a program of the invention are described in detail below with reference to a preferred embodiment illustrated in the accompanying drawings.

FIG. 1 is a block diagram conceptually illustrating an example of a configuration of an ultrasound diagnostic apparatus of the invention.

As illustrated in FIG. 1, an ultrasound diagnostic apparatus 10 has an ultrasound probe 12, a transmission section 14 and a receiving section 16 connected with the ultrasound probe 12, an analog-to-digital (A/D) converter 18, an element data storage 20, a data analyzer 23, an image generator 24, a display controller 26, a monitor 28, a controller 30, an operating section 32, and a storage 34.

In the example of FIG. 1, the transmission section 14, the receiving section 16, the A/D converter 18, the element data storage 20, the data analyzer 23, the image generator 24, the display controller 26, the monitor 28, the controller 30, the operating section 32, and the storage 34 configure the main apparatus body of the ultrasound diagnostic apparatus 10.

The ultrasound probe 12 (hereinafter called the probe 12) includes a transducer array 36 used in a normal ultrasound examination apparatus.

The transducer array 36 includes a plurality of elements, that is, ultrasound transducers arranged in a one-dimensional or two-dimensional array form. When taking an ultrasound image of an inspection object (hereinafter called a subject), these ultrasound transducers each transmit ultrasonic beams to the subject in accordance with a driving signal which is supplied from the transmission section 14, receive ultrasonic echoes from the subject, and output a reception signal. In the example, each of a predetermined number of ultrasound transducers forming a set thereof among a plurality of ultrasound transducers of the transducer array 36 generates each component of a single ultrasonic beam, and a set of the predetermined number of ultrasound transducers generates a single ultrasonic beam transmitted to the subject.

Each of the ultrasound transducers comprises an oscillator composed of a piezoelectric body and electrodes each provided on either end of the piezoelectric body. The piezoelectric body is composed of, for example, a piezoelectric ceramic represented by a lead zirconate titanate (PZT), a piezoelectric polymer represented by polyvinylidene fluoride (PVDF), or a piezoelectric monocrystal represented by lead magnesium niobate-lead titanate solid solution (PMN-PT).

When a pulsed or continuous-wave voltage is applied across the electrodes of the oscillator, the piezoelectric body expands and contracts in response to the applied voltage and pulsed or continuous wave ultrasonic waves are generated from each oscillator. In addition, the ultrasonic waves generated from each of the oscillators converge to be combined (that is, transmission focusing is performed on the ultrasonic waves) at set regions as focus according to a driving delay of each of the oscillators, thereby forming an ultrasonic beam.

In addition, the oscillators expand and contract due to ultrasonic echoes reflected from the subject being incident thereto and electric signals are generated according to the size of the expansion and contraction. The electric signals are output to the receiving section 16 as the reception signal.

The transmission section 14 has, for example, a plurality of pulsers and supplies a driving signal, that is, applies a driving voltage to each of the ultrasound transducers (oscillators) of the probe 12, for example.

For example, a delay amount of each driving signal is, in accordance with a sound velocity or the distribution of sound velocities set based on the transmission delay pattern selected according to a control signal from the controller 30, adjusted such that the ultrasonic beam component transmitted from a set of predetermined number of ultrasound transducers (hereinafter called ultrasound elements) of the transducer array 36. The adjusted driving signals are provided to a set of a plurality of ultrasound elements.

Furthermore, transmission focusing which adjusts a delay amount of the driving signal or an application timing of a driving voltage is performed so as to form an ultrasonic beam with an object of converging ultrasonic waves transmitted by a plurality of ultrasound transducers at set focus, and the driving signal is supplied to the ultrasound transducers. Here, the transmission delay pattern may be corrected according to an ambient sound velocity to be described below. Due to this, the desired ultrasonic beam is transmitted from the probe 12 (the transducer array 36) to the subject.

In accordance with the control signal from the controller 30, the receiving section 16 receives, from the subject, ultrasonic echoes generated by ultrasound elements of the transducer array 36 due to mutual action between ultrasonic beams and the subject, amplifies the reception signal, that is, an analog element signal for each ultrasound element, and outputs the amplified analog element signal to supply it to the A/D converter 18.

Here, the method of transmitting and receiving the ultrasonic waves in the ultrasound diagnostic apparatus 10 of the invention is basically the same as for a known ultrasound diagnostic apparatus.

Therefore, in a single transmission and reception of ultrasonic waves, that is, in transmission of a single ultrasonic beam and reception of ultrasonic echoes corresponding to this transmission, neither the number of ultrasound transducers which generate the ultrasonic waves, that is, the number of transmission openings nor the number of ultrasound transducers which receive the ultrasonic waves (where the receiving section 16 receives the reception signal), that is, the number of reception openings is limited as long as there is more than one of each. In addition, in a single transmission and reception, the number of openings may be the same or different in the transmission and the reception.

In addition, with ultrasonic beams adjacent in at least the azimuth direction (the arrangement direction of the ultrasound transducers), when transmission regions are overlapped, neither the number of times (number of sound rays) of the transmission and reception of the ultrasonic waves for forming one ultrasound image nor the intervals (that is, the density of the scanning lines) of the ultrasound transducers (center elements) in the center for the transmission and reception is limited. Accordingly, the transmission and reception of the ultrasonic waves may be performed with all of the ultrasound transducers corresponding to the region scanned with ultrasonic waves as the center elements, or the transmission and reception of the ultrasonic waves may be performed with ultrasound transducers at predetermined intervals, such as every two transducers or every four transducers, as the center elements.

The A/D converter 18 is connected with the receiving section 16 and analog/digital converts the analog reception signal which is supplied from the receiving section 16 into element data which is a digital reception signal.

The A/D converter 18 supplies A/D converted element data to the element data storage 20.

The element data storage 20 sequentially stores element data supplied from the A/D converter 18. In addition, the element data storage 20 stores information (for example, the depth of the reflection position of the ultrasonic waves, the density of the scanning lines, or a parameter indicating a visual field width) relating to the frame rate input from the controller 30 and position information such as coordinate positions of element data in the ultrasound image in association with each of element data.

Preferably, the element data storage 20 stores all of the element data corresponding to at least one ultrasound image (an ultrasound image of one frame) and does not erase element data of the ultrasound image before display or during display at least until the display of the ultrasound image is finished.

The data analyzer 23 is a section determining a sound velocity of ultrasonic waves of a region-of-interest in a subject using A/D converted element data in the A/D converter 18 or the element data storage 20. The determined sound velocity is supplied to the element data storage 20 and stored in the element data storage 20 in association with each of regions or each of position coordinates of the ultrasound image for each ultrasound image of one frame and for a predetermined number of frames which is at least one. Thus, when a sound velocity of a region-of-interest in a subject is determined, it is possible to use sound velocities of certain regions in the subject which are calculated previously.

The sound velocity of ultrasonic waves in the data analyzer 23 and a subject is to be described below in detail.

The image generator 24 generates reception data (sound ray signal) from element data supplied from the A/D converter 18 or the element data storage 20 under the control of the controller 30 and generates an ultrasound image from this reception data.

The image generator 24 has a phasing addition section 38, a detection processor 40, a DSC 42, an image processor 44, and an image memory 46.

The phasing addition section 38 performs reception focusing processing by carrying out matching addition on element data supplied from the A/D converter 18 or the element data storage 20, and generates reception data.

The distance to one reflection point in the subject is different for the respective ultrasound transducers. Therefore, even with ultrasonic echoes reflected at the same reflection point, the time for the ultrasonic echoes to arrive at each of the ultrasound transducers is different. According to a reception delay pattern selected by the controller 30, the phasing addition section 38 delays each of the reception data by an amount corresponding to the difference (the delay time) in the arrival time of the ultrasonic echoes for each of the ultrasound transducers, and carries out matching addition on the reception data to which the delay time is added, thereby digitally performing reception focusing processing and generating reception data.

The phasing addition section 38 supplies the generated reception data to the detection processor 40.

Here, in a case where the sound velocity of the ultrasonic waves in the subject is determined by the data analyzer 23 and supplied to the phasing addition section 38, the phasing addition section 38 performs reception focusing processing by correcting the delay time, the reception delay pattern, or the like using the sound velocity.

Here, in a case where the ambient sound velocity is not determined, the phasing addition section 38 performs reception focusing processing with a known method in which a reception delay pattern is used.

After carrying out correction of the attenuation due to the distance according to the depth of the reflection position of the ultrasonic waves with respect to the reception data generated by the phasing addition section 38, the detection processor 40 generates B mode image data which is tomographic image information (brightness image data) in the subject by carrying out an envelope detection processing.

The digital scan converter (DSC) 42 converts (raster conversion) the B mode image data generated by the detection processor 40 into image data corresponding to a normal television signal scanning system.

The image processor 44 carries out various necessary image processing such as gradation processing on the B mode image data input from the DSC 42 to create B mode image data for display. The image processor 44 performs at least one of output of the image processed B mode image data to the display controller 26 for display and storage of the image processed B mode image data in the image memory 46.

The image memory 46 is a known storage unit (a storage medium) which stores the B mode image data processed by the image processor 44. The B mode image data stored in the image memory 46 is read out to the display controller 26 for display on the monitor 28 as necessary.

The display controller 26 uses the B mode image data on which predetermined image processing is carried out by the image processor 44 to display a moving ultrasound image or a still ultrasound image on the monitor 28. The monitor 28, for example, includes a display apparatus such as a liquid crystal display (LCD) and displays a moving ultrasound image or a still ultrasound image under the control of the display controller 26.

The controller 30 controls each section of the ultrasound diagnostic apparatus 10 on the basis of instructions input from the operating section 32 by an operator.

In addition, the controller 30 supplies various types of information input by an operator using the operating section 32 to necessary units. For example, the controller 30 supplies information necessary for calculating the delay time used in the phasing addition section 38 of the image generator 24 to each section such as the transmission section 14, the receiving section 16, the element data storage 20, the image generator 24, and the display controller 26 as necessary.

The operating section 32 is for the operator to perform an input operation and can be formed of a keyboard, a mouse, a trackball, a touch panel, or the like.

In addition, the operating section 32 is provided with an input function for the operator to input various types of information as necessary. For example, the operating section 32 is provided with an input function for inputting information of the probe 12 (the ultrasound transducer); information relating to the generation of element data such as the transmission opening and the reception opening in the probe 12 (the transducer array), the number of element data to be superimposed, or the generation method; the focus position of the ultrasonic beam; and the like.

The above are input, for example, by selecting the photograph site (the examination site), selecting the image quality, selecting the depth of the ultrasound image to be photographed, or the like.

The operating section 32 is provided with a freeze button. When the freeze button is pressed during display of a B mode image, the B mode image displayed at the time of pressing the freeze button is displayed as a still image on the monitor 28. This enables the operator to observe the B mode image in detail through the still image.

The storage 34 stores information relating to an operation program for the controller 30 to execute control of each section of the ultrasound diagnostic apparatus 10, the transmission delay pattern and the reception delay pattern, and the generation of element data; information on the probe 12 input from the operating section 32; information on the transmission opening, the reception opening, and the focus position; information necessary for the controller 30 to operate and control the ultrasound diagnostic apparatus; and the like.

In the storage 34, it is possible to use a known recording medium such as a hard disk, a flexible disk, an magneto-optical disk (MO), a magnetic tape (MT), a random access memory (RAM), a compact disk read only memory (CD-ROM), or a digital versatile disk read only memory (DVD-ROM).

Here, in the ultrasound diagnostic apparatus 10, the data analyzer 23, the phasing addition section 38, the detection processor 40, the DSC 42, the image processor 44, the display controller 26, and the like are configured by a central processing unit (CPU) and an operation program causing the CPU to execute various processing. However, in the invention, these units may be configured by a digital circuit.

On the other hand, the data analyzer 23 determines the sound velocity of the ultrasonic waves in the subject using element data supplied from the A/D converter 18 or the element data storage 20.

FIG. 2 is a block diagram conceptually illustrating the configuration of the data analyzer 23.

As illustrated in FIG. 2, the data analyzer 23 includes a region-of-interest setting section 70, a transmission focus controller 72, a sound velocity searching range setting section 74, a focus index calculator 76, and a sound velocity determiner 78.

The region-of-interest setting section 70 sets the region-of-interest in the B mode image (in the ultrasound image) according to instructions from the controller 30.

In the data analyzer 23, the sound velocity of the subject is determined for every region-of-interest. The region-of-interest corresponds to calculation coordinates for which a sound velocity of ultrasonic waves is to be calculated in the ultrasound image.

In this example, the region-of-interest setting section 70 divides the whole display of the B mode image into a grid pattern and set each of the resulting segments as a region-of-interest.

The number of the segments resulting from the division (the number of grids) may be set in advance as a default value, or may be set to any value in at least one of the azimuth direction and depth direction by the operator. In the case where the number of the segments is set by default, a set value may vary depending on the image size and the site to be observed. Furthermore, it may be possible for the operator to select from a plurality of divisions set in advance.

Here, in the invention, the region-of-interest is not limited to each region of the grid into which the B mode image is divided.

For example, all of the pixels (the positions (regions) corresponding to all of the pixels) generated by the reception data (B mode image data) may be set as regions-of-interest. In other words, in a state where the screen is divided as described above, the screen may be divided into a grid corresponding to all of the pixels generated by the reception data.

Alternatively, instead of the entire screen, a part of the screen which is set in advance or selected from a plurality of choices may be divided into a grid and parts thereof individually set as regions-of-interest. Still alternatively, regions-of-interest may be set not for the whole display but for the region ROI set by the operator. Even when regions-of-interest are set for a part of the display or the region ROI, the division may be carried out in the same manner as that for the whole display. The operator may choose whether to set regions-of-interest for the whole display or the region ROI.

In addition, the form of the division is not limited to a grid, for example, in the case of a B mode image with a fan shape such as an ultrasound image according to a convex probe, the form of the division may also be set to a matching fan shape. In such a case, it is also possible to use each aspect described above.

Here, in the case where the image is greatly changed such as when the change value in the image feature amount exceeds a threshold, a case where the observation conditions such as observation magnification or observation depth are modified, or the like, a region-of-interest may be changed or updated. Alternatively, it may be possible for the operator to give an instruction for the changing or updating of the region-of-interest.

The region-of-interest setting section 70 also sets a focus (the position of the focus) in order to transmit (transmission focusing) the ultrasonic waves corresponding to the determination of the sound velocity with respect to a set region-of-interest.

The focus may be set in advance by default according to the site to be observed, the number of sound rays, the number of transmission and reception openings, the type of the probe 12, or the like. Alternatively, the operator may select a focus or instructs it through input. Still alternatively, it may be possible to allow selection between default setting or operator instructions.

The transmission focus controller 72 sends a transmission focusing instruction to the controller 30 for the transmission section 14 to perform the transmission focusing according to the region-of-interest and the focus set by the region-of-interest setting section 70.

The sound velocity searching range setting section 74 specifies a set sound velocity in order to perform reception focusing with respect to the reception data in the determining of the ambient sound velocity under the control of the controller 30, and the sound velocity searching range of a predetermined range is set. In the sound velocity searching range setting section 74, a starting sound velocity Vst and a finishing sound velocity Vend of a set sound velocity V (sound velocity searching range) are set.

In the example, regarding the set sound velocity, the method of setting a sound velocity searching range is different for a sound velocity value calculated first and a sound velocity value calculated secondly or later.

Regarding the sound velocity searching range for a sound velocity value calculated first, the set sound velocity including the starting sound velocity Vst and the finishing sound velocity Vend may be set in advance by default. Alternatively, only the starting sound velocity Vst and the finishing sound velocity Vend may be input by the operator as desired, while only the interval width therebetween (predetermined step sound velocity amount $\Delta V$) may be set by default. Still alternatively, the operator may input the starting sound velocity Vst, the finishing sound velocity Vend and the interval width as desired. When the set sound velocities and the interval width are set as default values, various set sound velocities may be set depending on the site to be observed, the sex or the like so that the operator can select an appropriate value.

Regarding the sound velocity value calculated first, the starting sound velocity Vst is set to 1400 m/s and the finishing sound velocity Vend is set to 1700 m/s, and based on the starting sound velocity Vst and the finishing sound velocity Vend, the set sound velocity is set at intervals of 40 m/sec which is the value of a predetermined interval width, for instance.

On the other hand, regarding the sound velocity value calculated secondly or later, the sound velocity searching range is set by the sound velocity searching range setting section 74 using a sound velocity obtained in a predetermined range with respect to at least one of space and time. A specific description will be given below.

Figure 3B:
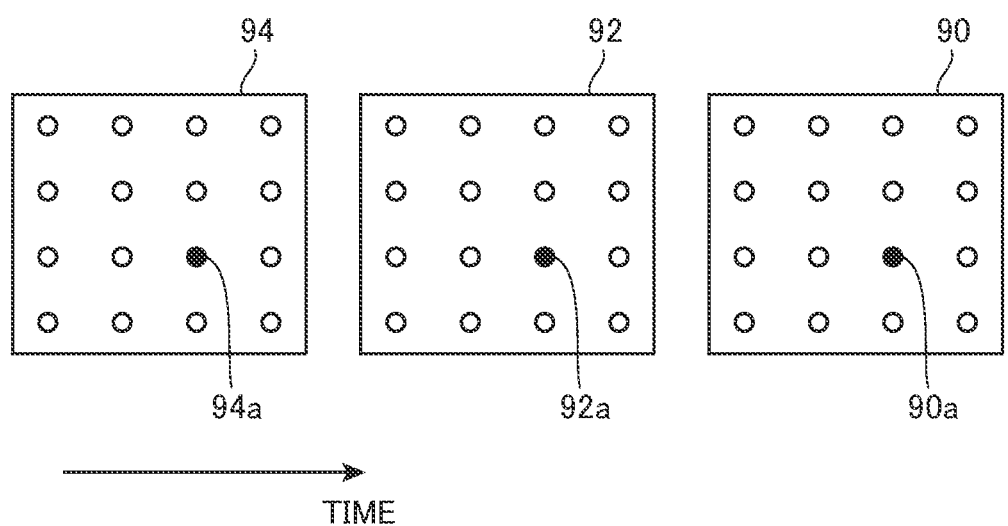
FIG. 3B is a schematic view for illustrating another example of resetting of a sound velocity searching range.

FIG. 3A is a schematic view for illustrating an example of resetting of a sound velocity searching range. FIG. 3B is a schematic view for illustrating another example of resetting of a sound velocity searching range.

For simplification, FIG. 3A illustrates the transducer array 36 including five ultrasound transducers arranged, and sound rays L1 to L5 are formed at the arrangement pitch of these ultrasound transducers. In this case, the sound velocity of a region 80 is obtained first, and then the sound velocity of a region 82 in the x direction (depth direction) of the sound ray L1 is obtained. Thereafter, proceeding to the sound ray L2 in the y direction, the sound velocities are obtained sequentially along the x direction.

When the sound velocity of the first region 80 in FIG. 3A is obtained, the sound velocity is obtained by a conventional method.

Regarding the region 82 deviating in the x direction, the sound velocity searching range is set in the sound velocity searching range setting section using the sound velocity of the region 80. The sound velocity searching range for the region 82 is set to a range of ±50 m/s relative to the sound velocity of the region 80, for example. When the sound velocity of the region 80 is 1500 m/s, for example, the sound velocity searching range of the region 82 is 1500±50 m/s.

When the sound velocity of a region 84 of the sound ray L3 is obtained, the sound velocity searching range can be set using the sound velocity of a region 84a, the sound velocity of a region 84b, the sound velocity of a region 84c, and the sound velocity of a region 84d, for example. The regions 84a to 84d are adjacent to the region 84 in a predetermined range. In this case, the used sound velocities are weighed depending on the distance between the region 84 for which the velocity is to be calculated and each of the regions 84a to 84d, so as to set the sound velocity searching range.

The adjacent regions are not limited to regions in a sound ray adjacent by one line, and the sound velocity searching range of the region 84 can be set using the sound velocity of the region 82 of the sound ray L1.

In each of the sound rays L1 to L5 in FIG. 3A, the sound velocity values are sequentially calculated in the x direction from the transducer array 36. In this case, in each of the sound rays L1 to L5, it is preferable to use the sound velocity value already calculated for the regions on the side of the transducer array 36.

Moreover, when a region R is set for an ultrasound image, and the sound velocity for regions other than a region 86 in the region R is required, the sound velocity searching range can be set using the sound velocities of regions in the region R. In addition, when the sound velocity of the region 86 in the region R is obtained, the sound velocity of the region 80 or the like can be used to set the sound velocity searching range.

When an ultrasound image is divided to a plurality of regions so as to include a region for which the sound velocity is to be determined, the sound velocity searching range can be set using the sound velocities of regions different from the region for which the sound velocity is to be determined among the plurality of regions.

In this manner, it is possible to set the sound velocity searching range using the sound velocities of pixels adjacent spatially. In addition, it is possible to set the sound velocity searching range using the sound velocities of regions adjacent temporally. The regions adjacent temporally indicates regions of previous frames for which the sound velocities are already calculated.

When the sound velocity is obtained for a region 90a of an ultrasound image 90 illustrated in FIG. 3B, the sound velocity searching range can be set using the sound velocity of a region 92a corresponding to the region 90a in an ultrasound image 92 of the previous frame. The previous frame may be a frame previous by at least one frame, and how previous the frame of an ultrasound image to be used is not particularly limited. The sound velocity searching range for the region 90a can be set using the sound velocity of a region 94a corresponding to the region 90a in an ultrasound image 94 of a frame prior to a frame of the ultrasound image 92.

For example, in moving tissue, the frame to be used is a frame previous by several frames. When tissue does not change, the frame to be used can be a frame further prior to the frame used for the moving tissue.

When the sound velocity of the previous frame is used, it is possible to further combine the above region adjacent spatially. That is, the sound velocity searching range can be set using the sound velocities of adjacent regions in the previous frame.

Moreover, when, regarding the region 90a of the ultrasound image 90 illustrated in FIG. 3B, the sound velocity searching range is set using the sound velocity of a region in an ultrasound image of a previous frame, it is also possible to use the sound velocity of a region corresponding to the sound velocity of at least, one region obtained by performing predetermined processing on sound velocities of regions of an ultrasound image of at least one predetermined previous frames. The predetermined processing is calculation of an average value of sound velocities of regions of an ultrasound image of one or more predetermined previous frames, or calculation of a median of sound velocities of the regions.

In this manner, the average value of sound velocities or the median of the sound velocities in a plurality of frames can be used to set the sound velocity searching range. For example, the average value of the sound velocity of the region 92a corresponding to the region 90a in the ultrasound image 92 of the frame and the sound velocity of the region 94a corresponding to the region 90a in the ultrasound image 94 of the frame can be used to set the sound velocity searching range for the region 90a of the ultrasound image 90.

In addition to the above, when the operator sets a region-of-interest (ROI), for example, the sound velocity searching range is preferably determined using a previous frame while emphasizing the time direction of ultrasound images. The setting of the region-of-interest can be detected by stopping of the ultrasound probe 12 and pressing of the freeze button, for example.

In the case of a moving subject, the sound velocity searching range is set based not on a frame adjacent temporally but on a frame adjacent spatially. In this case, the operator may determine which is to be used for setting by instructions through input. Furthermore, the ultrasound diagnostic apparatus 10 may determine which is used for setting by analyzing image features of the frames for which the velocities are already calculated.

For example, in the case of a still subject, the sound velocity searching range may be set to be narrow, while in the case of a moving subject, the sound velocity searching range may be set to be wide. When the sound velocity cannot be determined in a set sound velocity searching range, the sound velocity searching range may be expanded.

The focus index calculator 76 calculates the focus index of the reception data by performing reception focusing with respect to the reception date for each of a plurality of set sound velocities specified by the sound velocity searching range setting section 74 using element data of the A/D converter 18 or element data of the element data storage 20.

The sound velocity determiner 78 determines the ambient sound velocity of the region-of-interest based on the focus index for each of a plurality of set sound velocities.

Figure 4:
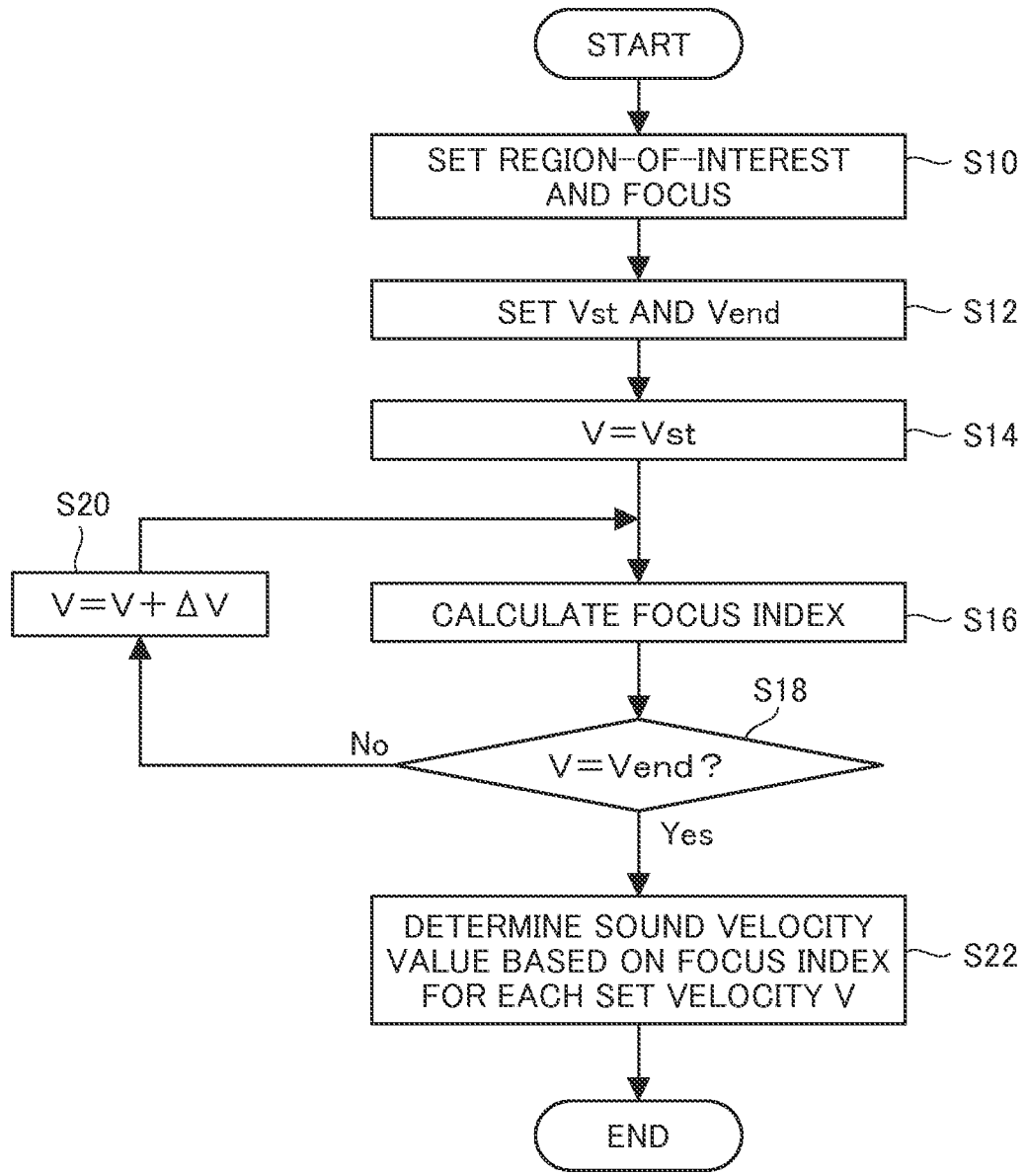
FIG. 4 is a flow chart for illustrating a sound velocity determining method of the data analyzer of the ultrasound diagnostic apparatus illustrated in FIG. 1.

The following will describe the method of determining a sound velocity of ultrasonic waves in a subject by the data analyzer 23. FIG. 4 is a flow chart for illustrating a sound velocity determining method of the data analyzer. Here, in the invention, the sound velocity determining method of the data analyzer 23 is not limited to this method and it is possible to use various sound velocity determining methods (methods of calculating the sound velocity) performed in the ultrasound diagnostic apparatus.

In the sound velocity determining method in the data analyzer 23, the region-of-interest setting section 70 sets a region-of-interest and focusing points according to instructions by the controller 30 (Step S10).

When element data is supplied, the data analyzer 23 stores element data in a predetermined site according to necessity. Also, the sound velocity searching range is set in the sound velocity searching range setting section 74, and the starting sound velocity Vst and the finishing sound velocity Vend of the set sound velocity V are set (Step S12). Furthermore, the starting sound velocity Vst is set to the set sound velocity V (Step S14).

Next, the focus index calculator 76 calculates the focus index of the reception data by performing reception focusing with respect to element data for each of a plurality of set sound velocities specified by the sound velocity searching range setting section 74 corresponding to each of the regions-of-interest (Step S16).

Specifically, for the reception data (the ultrasound image data) in the region-of-interest, the focus index calculator 76 calculates an integration value, a square integration value, a peak value, a degree of sharpness, a contrast value, a brightness value, a half width, a frequency-spectral integration value, a maximum value, a frequency-spectral integration value or squared integration value normalized with a direct current component, an autocorrelation value, or the like as the focus index.

Next, the sound velocity searching range setting section 74 determines whether the set sound velocity V has reached the finishing sound velocity Vend (Step S18). As a result of the determination, when the set sound velocity V is smaller than the finishing sound velocity Vend (No), the sound velocity searching range setting section 74 adds the predetermined step sound velocity amount ΔV, e.g., 40 m/s to the set sound velocity V (Step S20) and calculates the focus index of the region-of-interest (Step S16).

This routine is repeated and when it is determined that the set sound velocity V has reached the finishing sound velocity Vend (Yes), the sound velocity of the region-of-interest is determined in the sound velocity determiner 78 based on the focus index for each of the plurality of set sound velocities by setting the set sound velocity with the highest focus index as the sound velocity of the region-of-interest, or the like (Step S22). For example, by setting the brightness of the ultrasound image as the focus index, the sound velocity obtained by the ultrasound image with the highest brightness in the region-of-interest is set as the sound velocity of the region-of-interest.

That is, the sound velocity of the region-of-interest in the example is the average sound velocity of a region between the ultrasound probe 12 and the region-of-interest when the sound velocity from the probe 12 (the transducer array 36 (ultrasound transducers)) up to a certain region-of-interest is assumed to be constant.

The sound velocity obtained in the data analyzer 23 is supplied to the phasing addition section 38 and used to generate an ultrasound image. In this case, the obtained sound velocity value is an appropriate value. Accordingly, a favorable ultrasound image can be obtained.

The ultrasound diagnostic apparatus 10 can also display an ultrasound image using element data stored in the element data storage 20. In this case, the controller 30 switches the operation mode of the ultrasound diagnostic apparatus 10 to the element data storage 20 reproduction mode (hereinafter simply called reproduction mode) by instructions through input from the operating section 32.

In the reproduction mode, the controller 30 reads out element data from the element data storage 20 and supplies the element data to the phasing addition section 38 of the image generator 24. The subsequent operation is the same as the case of the B mode image. Thus, the detailed explanation thereof is omitted. In this manner, the ultrasound image (moving image or still image) based on element data stored in the element data storage 20 is displayed on the monitor 28.

The ultrasound diagnostic apparatus 10 is constituted basically as described above.

Below, with reference to the flow chart illustrated in FIG. 5, detailed description will be given of the method of determining the sound velocity in the ultrasound diagnostic apparatus 10.

Figure 5:
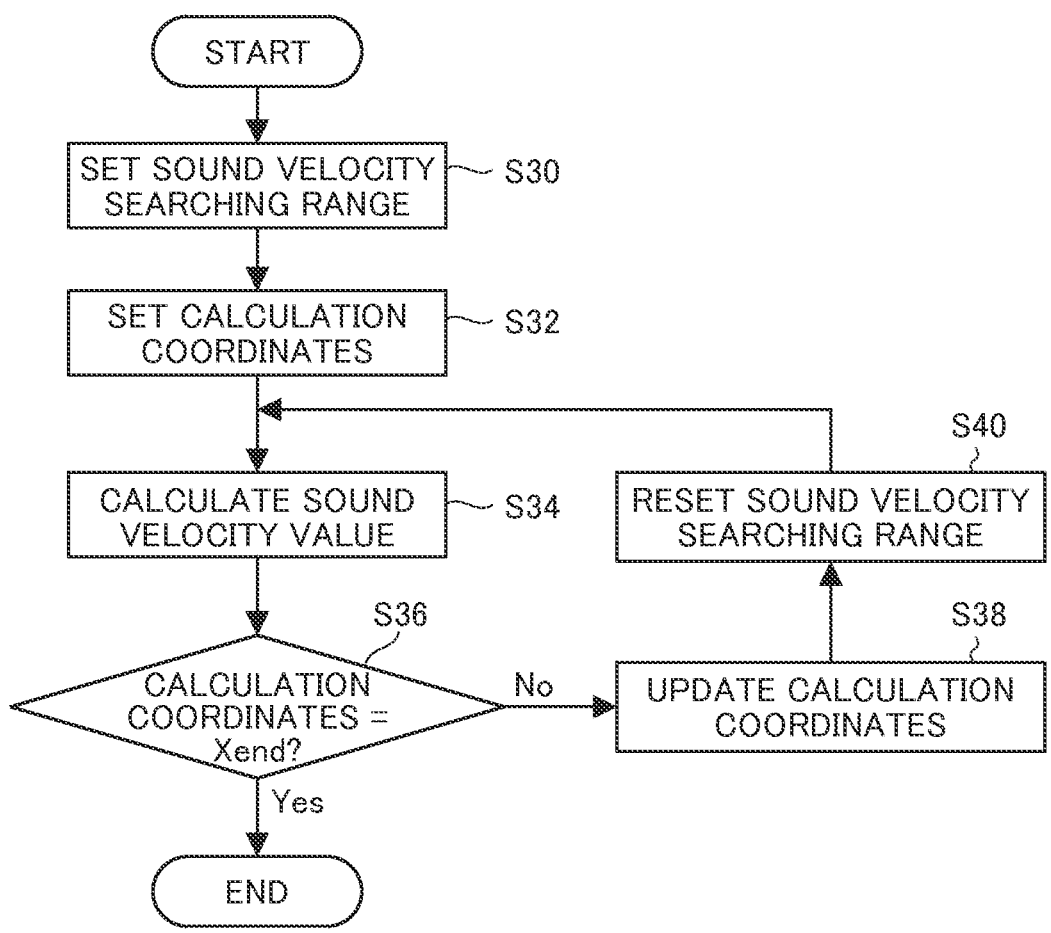
FIG. 5 is a flow chart for illustrating a sound velocity determining method of the ultrasound diagnostic apparatus.

FIG. 5 is a flow chart for illustrating a sound velocity determining method of the ultrasound diagnostic apparatus.

The program of the invention executes the following sound velocity determining method in a computer belonging to the ultrasound diagnostic apparatus 10.

Here, in the invention, the timing at which the sound velocity is determined (the update timing of the sound velocity) is not particularly limited and may be the same as for a known ultrasound diagnostic apparatus. For example, the sound velocity may be determined only once in accordance with instructions for start of measurement, or may be determined when the image greatly varies (when the change value in the image feature amount exceeds a threshold, or the like). Alternatively, the sound velocity may be determined in units of a predetermined number of frames determined appropriately or every time predetermined time has passed. Still, alternatively, the sound velocity may be determined according to instructions through input by the operator. In addition, two or more timings at which the sound velocity is determined may be selected appropriately.

In the ultrasound diagnostic apparatus 10, when the sound velocity is determined, the range in which the sound velocity is determined in the ultrasound image, and the position at which the sound velocity is calculated (region-of-interest) in the determined range, that is, the calculation coordinates are set. Then, the region-of-interest and the focus are set in the region-of-interest setting section 70 according to instructions from the controller 30.

As illustrated in FIG. 5, the sound velocity searching range of the calculation coordinates for which the sound velocity is to be calculated first (hereinafter called initial coordinates) is set (Step S30). Here, the sound velocity searching range is set to 1400 to 1700 m/s, and the interval is set to 40 m/s, for example. Next, initial coordinates and final coordinates in the determined range are set (Step S32).

Next, the sound velocity of the initial coordinates is calculated using the method illustrated in the above FIG. 3 (Step S34). In this case, according to the setting of the region-of-interest, the transmission focus controller 72 sends transmission focusing instructions to the controller 30 so that the transmission section 14 executes the transmission focusing with respect to the set region-of-interest and focus.

Accordingly, the transmission section 14 transmits the ultrasonic beam to the subject by driving the probe 12 (the corresponding ultrasound transducers (elements) in the transducer array 36), the ultrasonic echoes reflected by the subject are received by the elements, and an analog reception signal is output to the receiving section 16 from the ultrasound transducers (elements).

The receiving section 16 carries out a predetermined processing such as amplification on the analog reception signal and supplies the result to the A/D converter 18. The A/D converter 18 A/D converts the analog reception signal supplied from the receiving section 16 and sets the signal as element data which is a digital reception signal. Element data is stored in the element data storage 20. The data analyzer 23 determines the sound velocity of the ultrasonic waves in the subject using element data supplied from the A/D converter 18 or the element data storage 20. Here, in the flowchart of FIG. 4, the smallest value and the maximum value in the sound velocity searching range are set in Step S12. Subsequently, the sound velocity of the initial coordinates is determined in Step S14 to Step S22 where the sound velocity is determined as described above in detail.

Next, as illustrated in FIG. 5, whether the calculation coordinates are final coordinates is determined (Step S36). Unless it is determined in Step 36 that the calculation coordinates are final coordinates, the calculation coordinates are updated (Step S38). Then, the sound velocity searching range is reset with respect to the updated calculation coordinates (Step S40).

As the method of resetting the sound velocity searching range, the sound velocity of the initial calculation coordinates is used for the second calculation coordinates. For example, when the initial sound velocity value is 1500 m/s, the sound velocity searching range of the second calculation coordinates is set to 1500±50 m/s.

For the third or later calculation coordinates, the sound velocity searching range can be reset using the above method. When the sound velocity of the ultrasound image of at least one frame is already calculated, the sound velocity of a previous frame can be used, as described above.

After resetting the sound velocity searching range, the sound velocity of the updated calculation coordinates is determined (Step S34).

Next, whether the calculation coordinates are final coordinates is determined (Step S36). Unless it is determined that the calculation coordinates are final coordinates, the calculation coordinates are updated (Step S38), the sound velocity searching range is reset (Step S40), and the sound velocity of the updated calculation coordinates is determined (Step S34). This sequence of processes is repeated until the calculation coordinates are determined to be final coordinates in the calculation range of the sound velocity of the ultrasound image, and the sound velocities of all calculation coordinates are calculated. The calculated velocity is stored in the element data storage 20 in association with each region of the ultrasound image for each ultrasound image of one frame and for a predetermined number of frames. The calculated velocities are used to generate an ultrasound image. They are appropriate values, and thus a favorable ultrasound image can be obtained.

In the example, regarding the second or later calculation coordinates, the optimum sound velocity searching range can be set by resetting the sound velocity searching range based on the velocity calculated previously, and the sound velocity searching range can be reduced as compared with the case where the sound velocity searching range is set comprehensively. This is effective for a region such as a liver having a small part where the sound velocity value greatly varies locally in the subject, for example.

Regarding the second or later calculation coordinates, the sound velocity searching range is reset based on the sound velocities calculated in the previous frames, which reduces the sound velocity searching range. This is effective when the variation of sound velocity values between frames is small, for example.

Furthermore, the sound velocity searching range is reset based on the average value or the median for each region among the sound velocities obtained in a plurality of previous frames, whereby the robust sound velocity value can reduce the sound velocity searching range.

In this manner, it is possible to reduce time required for calculating a sound velocity and improve a frame rate.

The invention is constituted basically as described above. Above, the ultrasound diagnostic apparatus, the ultrasound image generation method, and a recording medium recording the program of the invention have been described; however, the invention is not limited to the examples described above and various improvements or modifications may be made within a range which does not depart from the gist of the invention as a matter of course.

What is claimed is:

1. An ultrasound diagnostic apparatus acquiring an ultrasound image for examining an inspection object using an ultrasonic beam, the ultrasound diagnostic apparatus comprising:
    a sound velocity determiner configured to determine an ambient sound velocity with respect to each of a plurality of regions in the inspection object; and
    a sound velocity searching range setting section configured to set a sound velocity searching range within which the sound velocity determiner searches in order to determine the ambient sound velocity of each of the plurality of regions,
    wherein, upon determination of a first estimated ambient sound velocity of each of the plurality of regions, the sound velocity searching range setting section sets a first sound velocity searching range, and the sound velocity determiner searches one or more sound velocities within the first sound velocity searching range to determine a second estimated ambient sound velocity for each of the plurality of regions, and
    wherein, after determining the second estimated ambient sound velocity for each of the plurality of regions, the sound velocity searching range setting section sets a second sound velocity searching range for one of the plurality of regions based on the second estimated ambient sound velocity of another of the plurality of regions, the second sound velocity searching range being different from the first sound velocity searching range, and
    the sound velocity determiner searches one or more sound velocities within the second sound velocity searching range in the one of the plurality of regions to determine a third estimated ambient sound velocity for the one of the plurality of regions,
    wherein the second sound velocity searching range has an upper limit and a lower limit, and wherein the center value of the second sound velocity searching range is the average value of the upper limit and the lower limit, and
    wherein the central value of the second sound velocity searching range is the same as the second sound velocity of the another of the plurality of regions.

2. The ultrasound diagnostic apparatus according to claim 1,
    wherein the another of the plurality of regions is adjacent to the one of the plurality of regions.

3. An ultrasound image generation method for acquiring an ultrasound image for examining an inspection object using an ultrasonic beam, the ultrasound image generation method comprising the steps of:
    determining a first estimated ambient sound velocity with respect to each of a plurality of regions in the inspection object; and
    setting a first sound velocity searching range in order to determine a second estimated ambient sound velocity of each of the plurality of regions,
    wherein, upon determining the first estimated ambient sound velocity of each of the plurality of regions, searching one or more sound velocities within the first sound velocity searching range and determining the second estimated ambient sound velocity for each of the plurality of regions, and
    wherein, upon determination of the second estimated ambient sound velocity for each of the plurality of regions, setting a second sound velocity searching range for one of the plurality of regions based on the second estimated ambient sound velocity of another of the plurality of regions, the second sound velocity searching range being different from the first sound velocity searching range, searching one or more sound velocities within the second sound velocity searching range in the one of the plurality of regions to determine a third estimated ambient sound velocity for the one of the plurality of regions,
    wherein the second sound velocity searching range has an upper limit and a lower limit, and wherein the center value of the second sound velocity searching range is the average value of the upper limit and the lower limit, and wherein the central value of the second sound velocity searching range is the same as the second estimated ambient sound velocity of the another of the plurality of regions.

4. The ultrasound image generation method according to claim 3, wherein the another of the plurality of regions is adjacent to the one of the plurality of regions.

5. An ultrasound diagnostic apparatus acquiring an ultrasound image for examining an inspection object using an ultrasonic beam, the ultrasound diagnostic apparatus comprising:

a memory storing a first sound velocity searching range; and a processor configured to determine a sound velocity with respect to each of a plurality of regions in the inspection object, the processor being further configured to set a sound velocity searching range within which a sound velocity is searched in order to determine the sound velocity for each of the plurality of regions, wherein, upon determination of a first estimated ambient sound velocity for each of the plurality of regions, the processor reads out the first sound velocity searching range from the memory and sets the sound velocity searching range as the first sound velocity searching range and searches one or more sound velocities within the first sound velocity searching range to determine a second estimated ambient sound velocity for each of the plurality of regions, wherein, after determining the second estimated ambient sound velocity for each of the plurality of regions, the processor sets a second sound velocity searching range for one of the plurality of regions based on the second estimated ambient sound velocity of another of the plurality of regions, the second sound velocity searching range being different from the first sound velocity searching range, and wherein the processor searches one or more sound velocities within the second sound velocity searching range and in the one of the plurality of regions to determine a third estimated ambient sound velocity for the one of the plurality of regions, wherein the second sound velocity searching range has an upper limit and a lower limit, and wherein the center value of the second sound velocity searching range is the average value of the upper limit and the lower limit, and wherein the central value of the second sound velocity searching range is the same as the second estimated ambient sound velocity of the another of the plurality of regions.

* * * * *